United States Patent [19]
Daoud et al.

[11] Patent Number: 5,123,275
[45] Date of Patent: Jun. 23, 1992

[54] AIR IN-LINE SENSOR SYSTEM

[75] Inventors: Adib G. Daoud; Fred W. Bacher, both of San Diego, Calif.

[73] Assignee: IVAC Corporation, San Diego, Calif.

[21] Appl. No.: 624,406

[22] Filed: Dec. 7, 1990

[51] Int. Cl.$^5$ ............................................. G01N 29/02
[52] U.S. Cl. .............................. 73/19.03; 128/DIG. 13
[58] Field of Search ................................ 73/19.03, 632; 128/DIG. 13

[56] References Cited

U.S. PATENT DOCUMENTS

| | | | |
|---|---|---|---|
| 3,376,438 | 4/1968 | Colbert | 73/632 X |
| 3,630,481 | 12/1971 | McGay | 251/6 |
| 3,893,468 | 7/1975 | McPhee | 137/1 |
| 3,898,637 | 8/1975 | Wolstenholme | 340/239 |
| 3,900,184 | 8/1975 | Burke et al. | 251/6 |
| 3,921,622 | 11/1975 | Cole | 128/2 |
| 3,960,149 | 6/1976 | Bujan | 128/214 |
| 3,974,681 | 8/1976 | Namery . | |
| 4,068,521 | 1/1978 | Cosentino et al. | 73/19 |
| 4,312,341 | 1/1982 | Zissimopoulos et al. | 128/214 |
| 4,344,429 | 8/1982 | Gupton et al. | 128/214 |
| 4,367,736 | 1/1983 | Gupton | 128/214 |
| 4,418,565 | 12/1983 | St. John | 73/19 |
| 4,607,520 | 8/1986 | Dam | 73/19.03 X |
| 4,651,555 | 3/1987 | Dam | 73/19.03 |
| 4,764,166 | 8/1988 | Spani | 604/63 |
| 4,821,558 | 4/1989 | Pastrone et al. | 73/19.03 |

FOREIGN PATENT DOCUMENTS 2240342 3/1974 Fed. Rep. of Germany ..... 73/19.03

Primary Examiner—Hezron E. Williams
Assistant Examiner—Joseph W. Roskos
Attorney, Agent, or Firm—Fulwider, Patton, Lee & Utecht

[57] ABSTRACT

A sensor system has a two-housing arrangement, each housing of which contains a transducer. One housing includes the transmitter transducer and a flat engaging surface for pressing against the fluid line and deforming it. The other housing includes the receiver transducer mounted so that it is coupled to the bottom of a rectangular U-shaped channel for receiving the fluid line. A spring biases the flat surface of the first housing into contact with the fluid line and deforms the fluid line into the shape of the channel so that the fluid line fills the channel. The channel is shaped to force the fluid line into a general rectangular shape as it is pressed into the channel by the flat surface. Two walls of the deformed fluid line are oriented in a direction perpendicular to the flat engaging surface of the first housing and provide an opposing force to the flat surface. The fluid line stiffness and pressure of the fluid within act as an opposing spring to limit the travel of the transmitter transducer housing to result in firm and continuous contact between the transducers and the fluid line. A stop mechanism prevents the two housings from contacting.

20 Claims, 4 Drawing Sheets

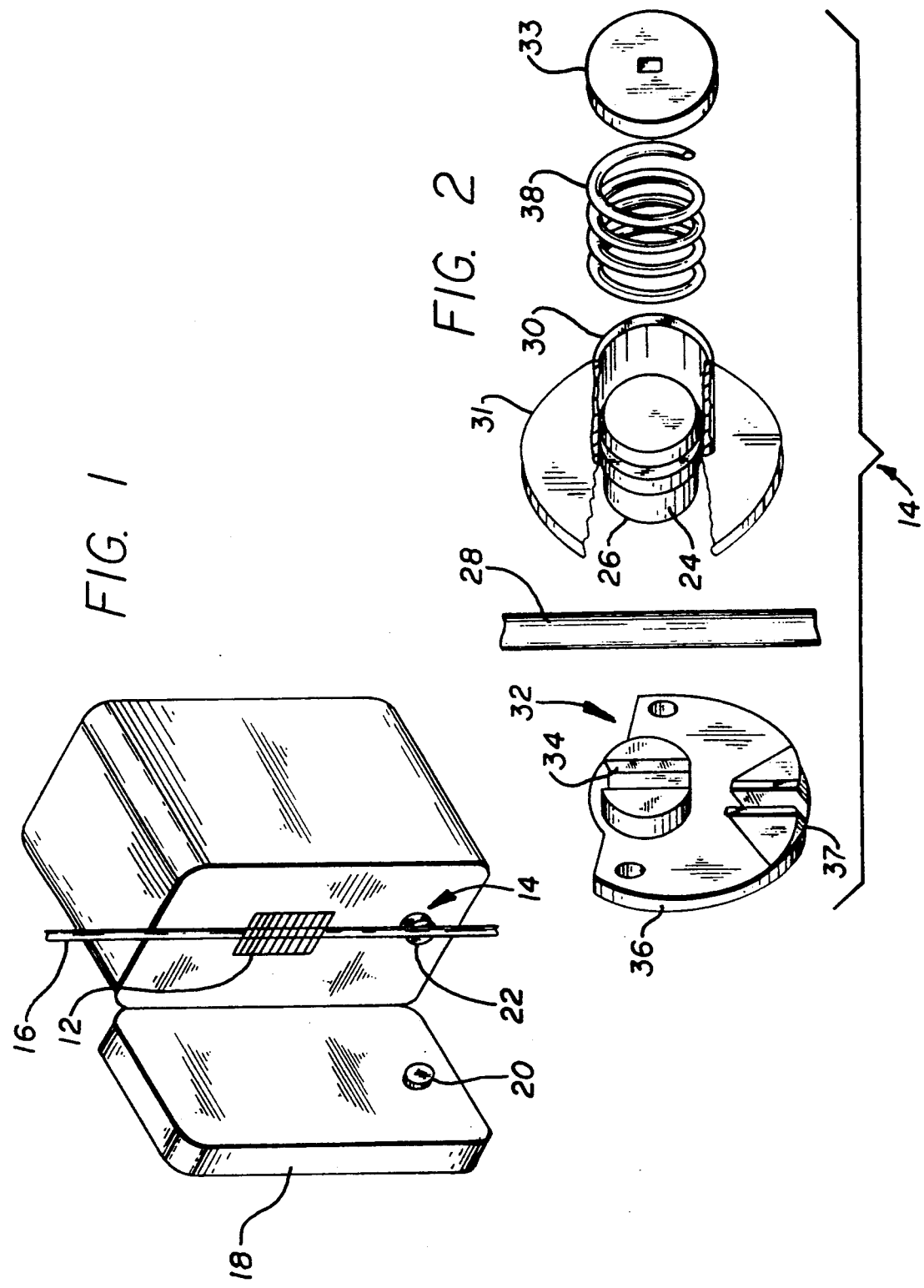

AIR IN-LINE SENSOR SYSTEM

BACKGROUND

The invention is related generally to monitoring systems, and more particularly, to detecting discontinuities in a line of flowing fluid.

The infusion of fluids such as parenteral fluids into the human body is usually accomplished by means of an administration set and a metering apparatus which controls the rate of flow of the fluid through the set. Peristaltic pumps are commonly used to impact pressure to infuse the fluids as well as to meter the fluid flow.

A problem arising with the infusion of fluid into the human body is the possibility of an air embolism. While relatively small bubbles in the infused fluid may be harmless, a large enough bubble of air may result in an air embolism in the patient with fatal consequences. Dissolved gases in a liquid being infused may be released as bubbles as the liquid is subjected to pressure from a pump. Thus, monitoring for the presence of bubbles in the fluid line is a common practice where pumps are used. The monitoring is performed downstream of the pump.

Ultrasonic sensing systems are commonly used as air-in-line sensors. However, one requirement of ultrasonic systems is good ultrasonic conduction between the walls of the fluid line and the ultrasonic transducers. Continuous contact is required. A transmitter transducer is placed opposite the fluid line from the receiver transducer and energy is transmitted between the two through the fluid line. Air has a substantially different acoustic impedance in comparison to liquid and air in a liquid flowing in the fluid line between the two transducers will be detected by the substantial change in the amount of ultrasonic energy received by the receiver. However, the ultrasonic sensor cannot distinguish between an air gap caused by poor contact between the transducer and the fluid line and an air bubble in the fluid flowing in the fluid line. Thus, contact directly affects sensor performance.

With one piece ultrasonic sensor housings, ultrasonic energy tends to find its way through the sensor housing from one transducer to the other without passing through the fluid line. This results in an undersirable background noise level which reduces the sensitivity of the sensor system. Accordingly, a two sensor housing arrangement is preferred. Each sensor housing has a transducer and the two sensor housings have an air gap between them when they are engaged with each other which acts to block the transmission of ultrasonic energy from reaching the receiver transducer unless it proceeds through the fluid line being monitored.

A design goal of two-housing arrangements for ultrasonic sensors in the medical field is ease of use. Administration sets are typically disposable and the ultrasonic sensor unit should be able to accept numerous sets. Correct placement of the fluid line between the two housing parts should be easy and quick to accomplish. Where the sensor is co-mounted with a peristaltic pump, ease of tubing engagement with the air-in-line sensor after pump engagement is desirable. Means to hold the fluid line in position once engaged should be provided so that operation of an associated pump or patient movement do not cause the fluid line to dislodge from the sensor and provide a false alarm. Additionally, the two-part housing should have the ability to compensate for tubing dimensional tolerances and size changes due to differing manufacturing tolerances, temperature and pressure variations and other factors which may affect the tubing. A simple engagement system is preferred but also one which will result in the tubing being firmly engaged by the transducers so that good transducer/tubing contact exists with the result of reduced noise levels. However, the engagement of the tubing with the transducers should not be to such an extent that fluid flow is excessively restricted.

Hence those concerned with fluid line monitoring have recognized that it would be benefical to provide a versatile fluid monitoring system and method useful for detecting air in the line, which can be used with disposable administration sets under varying conditions, yet is accurate and does not excessively restrict fluid flow. The present invention fulfills these needs.

SUMMARY OF THE INVENTION

The present invention provides for fluid line monitoring by an ultrasonic sensor system having a two-housing arrangement, each housing of which contains an ultrasonic transducer. An air gap is maintained between the housing parts and this gap is controlled to some extent by the stiffness of the fluid line itself.

One housing includes the transmitter transducer and a flat engaging surface for pressing against the fluid line and deforming it. The other housing includes a rectangular U-shaped channel for receiving the fluid line and the receiver transducer mounted so that it is coupled to the bottom of the channel. A spring biases the flat surface of the first housing into contact with the fluid line. The flat surface of the first housing presses against the fluid line and deforms it into the shape of the channel so that the fluid line fills the channel. This deformation causes the fluid line to make firm contact with the bottom of the channel where the transducer is located and with the flat engaging surface to which the other transducer is coupled.

In addition to its association with a transducer, the channel is shaped to force the fluid line into a general rectangular shape as it is pressed into the channel by the flat surface. The result is that two walls of fluid line are formed and are oriented in a direction perpendicular to the flat engaging surface of the first housing. Because the walls of the channel restrict the fluid line from expanding outward and the pressure of the fluid in the fluid line restricts the fluid line from moving inward, pressure is exerted by the deformed fluid line against the flat engaging surface in opposition to the biasing spring. The stiffness of the fluid line and the depth of the channel have a direct effect on the amount of force provided in opposition to the bias spring. By this arrangement, the fluid line is not permitted to merely collapse as a result of pressure from the flat surface, firm and continuous contact between the transducers and fluid line is assured regardless of changes in the tubing size caused by temperature, pressure or other factors.

An air gap is maintained between the two housings. A mechanical stop is included in one embodiment to prevent the two housings from contacting each other, thereby preserving a minimum air gap. The fluid line stiffness acts as an opposing spring to limit the travel of the transmitter transducer housing. Thus the positions of the two housings in relation to each other are force limited by virtue of the stiffness of the fluid line rather than travel limited as in many other designs. This fluid line spring action limits the movement of the housings in relation to each other so that the mechanical stop is not engaged, thus firm and continuous contact between the transducers and the fluid line is maintained.

The invention provides for ease in loading the fluid line into the sensor because of the channel formed in one housing. This channeled housing facilitates the initial location of the fluid line in the sensor and opposes disengagement of the fluid line from the sensor due to patient movement. The possibility of false alarms is thus lessened. The door of the instrument may contain the second housing with the flat engaging surface and the transmitter transducer. Closing the door results in the flat housing deforming the fluid line into the channeled housing thus controlling its position and causing firm contact with both transducers.

Other aspects and advantages of the invention will become apparent from the following detailed description and the accompanying drawings, illustrating by way of example the features of the invention.

BRIEF DESCRIPTION OF THE DRAWINGS

FIG. 1 presents a perspective view of an air-in-line sensor mounted below a peristaltic pump with a fluid line engaged with both in an infusion instrument;

FIG. 2 is an exploded perspective view of a two housing arrangement in an air-in-line sensor in accordance with the principles of the invention;

DETAILED DESCRIPTION OF THE PREFERRED EMBODIMENTS

Figure 3:
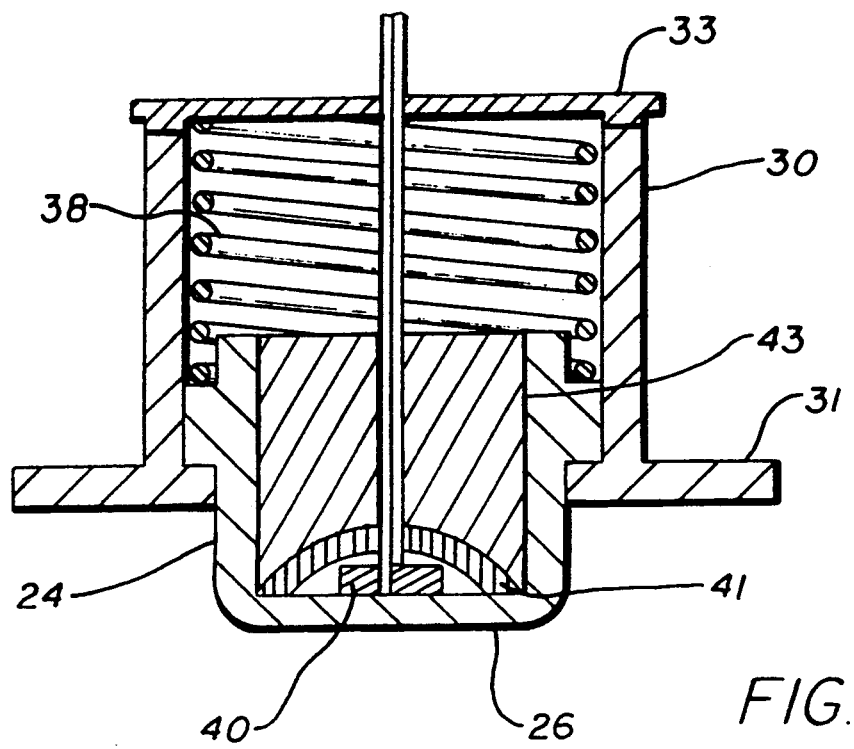
FIG. 3 is a cross-sectional view of the first housing of the sensor of FIG. 2 showing the flat engaging surface and the biasing spring.

Referring now to the drawings with more particularly, wherein like reference numerals designate like or corresponding elements among the several views, there is shown in FIG. 1 an infusion apparatus 10 including a peristaltic pump 12 and an air-in-line sensor 14 for use with a fluid line 16. Typically, the infusion apparatus 10 is suspended so that when the fluid line 16 is engaged with the peristaltic pump 12, gravity will cause the fluid line to fall over the air-in-line sensor 14. The fluid flow is from the top to the bottom of the apparatus 10 so that the air-in-line sensor 14 senses the fluid after it has been operated on by the pump 12. The apparatus 10 includes a door 18 shown in the open position in FIG. 1, and that door includes a first housing 20 of the air-in-line sensor 14 which engages the second housing 22 of the air-in-line sensor 14 when the door is closed.

Referring now to FIG. 2, an air-in-line sensor 14 in accordance with the principles of the invention is shown having two housings. Each housing includes an ultrasonic transducer as will be described in more detail below. The first housing 24 includes a flat engaging surface 26 for engaging the fluid line 28. The first housing 24 is movable in a mounting housing 30 and is biased by a spring 38 towards the fluid line 28 in this embodiment so that the flat surface 26 will contact the fluid line 28 and deform it. A retaining cap 33 is used to confine the spring 38 in the mounting housing 30 to press against the first housing 24. The mounting housing 30 is also shown as including a mounting flange 31.

Figure 4:
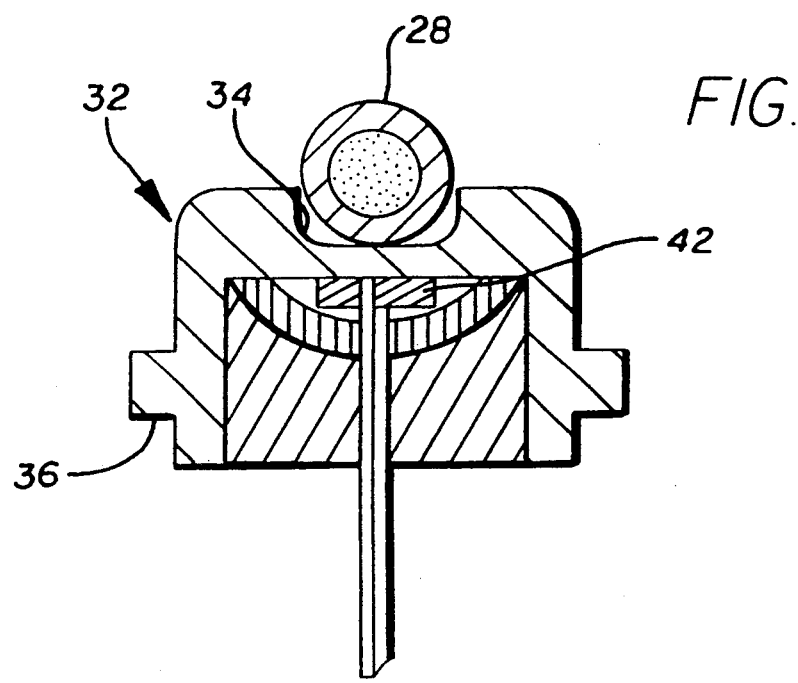
FIG. 4 is a cross-sectional view of the second housing of the sensor of FIG. 2 showing the channel formed in the housing in accordance with the principles of the invention and a fluid line positioned in the channel.

The second housing 32 includes a rectangular U-shaped channel 34, the cross section of which is larger than the cross section of the fluid line when the fluid line is in its relaxed configuration as shown in FIG. 4. As with the first housing 24, the second housing 32 contains an ultrasonic transducer as will be described in more detail below. The channel 34 of the second housing 32 is useful to guide the fluid line 28 into the correct position in relation to the ultrasonic transducer mounted within the second housing 32. Also, in the application shown in FIG. 1, the channel 34 is useful in guiding the fluid line into the correct position in relation to the peristaltic pump 12 so that when the door 18 is closed, the fluid line 16 is properly engaged with both the pump 12 and the sensor 14.

The second housing 32 also includes a mounting flange 36 and a tubing guide 37. The tubing guide 37 includes a channel aligned with the channel 34 of the sensor and is useful in correctly locating the tubing in the sensor. Also, the channel of the tubing guide and the channel of the sensor are both useful in retaining the fluid line engaged with the sensor when the fluid line is subjected to movement such as tugging resulting from patient movement. As will be described in more detail below, the spring loading of one housing toward the other housing also contributes to keeping the fluid line in the channel under conditions such as patient movement. This feature lessens the possibility of false air-in-line alarms.

Referring now to FIG. 3, a first housing 24 in accordance with the principles of the invention is shown in cross-sectional view. The housing includes the flat engaging surface 26 also shown in FIG. 2. A mounting housing 30 includes the first housing 24 slidably located therein and a spring 38 which acts to bias the first housing 24 and the flat engaging surface 26 outward from the mounting housing 30. The cap 33 retains the spring 38 in the mounting housing 30 to bias the first housing outward.

The first housing 24 includes an ultrasonic transducer 40 which, in this embodiment, is in direct contact with the back of the flat surface 26. Behind the transducer 40 is mounted backing material 41 such as cork or poron or other material useful for absorbing sound. Behind the backing material is a filler 43, such as epoxy used to hermetically seal the transducer. The backing material is used to isolate the transducer from the filling material and allow the transducer to vibrate. Electrical feeds for the transducer are shown traversing the housing 24 in its approximate center; however, this is for purposes of illustration only. The feeds may be located elsewhere. The size of the transducer is selected so that ultrasonic energy is directed through the inside of the fluid line and not the fluid line itself. The mounting flange 31 may be used to fix the housing 24 to the door of an infusion or other apparatus, such as in the arrangement shown in FIG. 1. Other mounting means may be used.

One example of an ultrasonic transducer usable in the housings is a piezoelectric crystal; however, other devices may be used. Additionally, although shown as being mounted in direct contact with the back of the flat surface, other mounting methods of the transducer may be used. The arrangement shown in FIG. 3 is for illustration purposes only.

Referring now to FIG. 4, the second housing 32 is shown in cross-section. A rectangular U-shaped channel 34 is formed into the housing 32. An ultrasonic transducer 42 is mounted immediately below the channel 34 and is in direct contact with the housing, as in the first housing 24. As also in the first housing 24, a backing material is disposed behind the transducer 42 and a filler material behind that in this embodiment. The electrical feeds are centrally located in the embodiment shown in FIG. 4 but may be mounted elsewhere. A mounting flange 36 may be used to rigidly mount the housing 32 into an apparatus as is shown in FIG. 1. Also shown is a compliant fluid line or tubing 28 disposed in place in the channel 34. The tubing 28 is in its relaxed state with fluid flowing through it.

Figure 5:
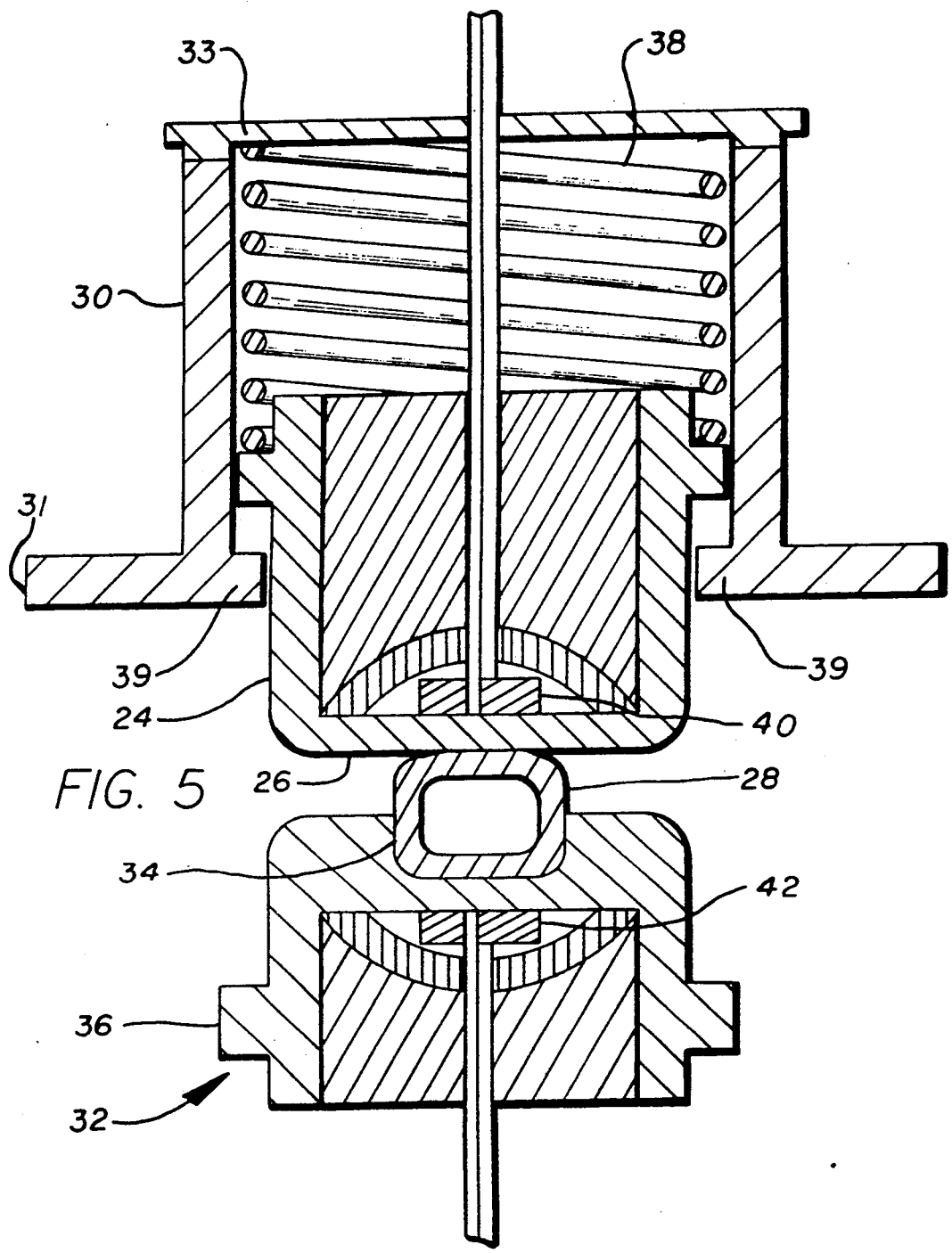
FIG. 5 is a cross-sectional view of an air-in-line sensor having a two-housing arrangement which has engaged a fluid line and is monitoring the fluid flow in the fluid line.

Referring now to FIG. 5, there is shown in cross-section the housings 24 and 32 in an engaged position with the fluid line 28 and with each other. The flat engaging surface 26 has contacted the fluid line 28 and exerted enough pressure against the fluid line 28 to deform it into the rectangular U-shaped channel 34 to fill the channel. This pressure from the flat engaging surface 26 and the particular shape of the channel 34 into which the fluid line 28 is pressed causes the fluid line 28 to assume a somewhat rectangular shape. The bottom of the channel is flat to provide for continuous contact with the coupling surface to the associated transducer 42. The height of the walls of the channel is selected to cause the fluid line to have two sections which are approximately perpendicular to the flat engaging surface 26. These sections will provide an opposing force to the flat engaging surface which is dependent upon the stiffness of the fluid line and the pressure of fluid within. This opposing force will result in the two housings 24 and 32 having an air gap between them while at the same time providing for continuous and firm contact between the fluid line and the transducers in the housings. This deformed shape has been found to result in a fluid line which is open enough to permit unobstructed fluid flow yet provides for good contact with the critical transducer coupling surfaces.

In one embodiment in an infusion apparatus, the channeled housing 32 is mounted in the infusion apparatus body while the mounting housing 30 with the flat engaging surface housing 24 is mounted on the door which is movable in relation to the body. The door is typically mounted so that it swings into position in relation to the body and locks in position. Thus, the mounting housing 30 will always be at a certain distance from the channeled housing when the door is closed. This distance is set in dependence upon the size of the smallest tubing usable in the sensor and the amount of protrusion possible of the first housing 24 from the mounting housing 30. In the embodiment of FIG. 5, the mounting housing 30 includes a mechanical stop 39 to prevent the first housing from contacting the channeled housing. Therefore, as long as the fluid line is in the channel, fluid can flow through the line and the sensor will not occlude the fluid line. The mechanical stop also assures a minimum air gap between the two housings although in the case where a fluid line is engaged in the housing, the stiffness of the fluid line and pressure within will cause a greater air gap to exist.

As shown in FIG. 5, the force developed by the tubing 28 has caused some compression of the bias spring 38. The bias spring is selected so that it will have enough force to flatten the tubing and deform it into the channel for good acoustic coupling of the transducers with the tubing, yet will not overly deform the tubing to restrict fluid flow or cause poor transducer contact. Thus, the strength of the spring is selected after consideration of the tubing stiffness and fluid pressure in the tubing.

In one embodiment, the transducer 40 of the first housing 24 was used as the transmitter and the transducer 42 of the second housing 32 was used as the receiver.

Figure 6:
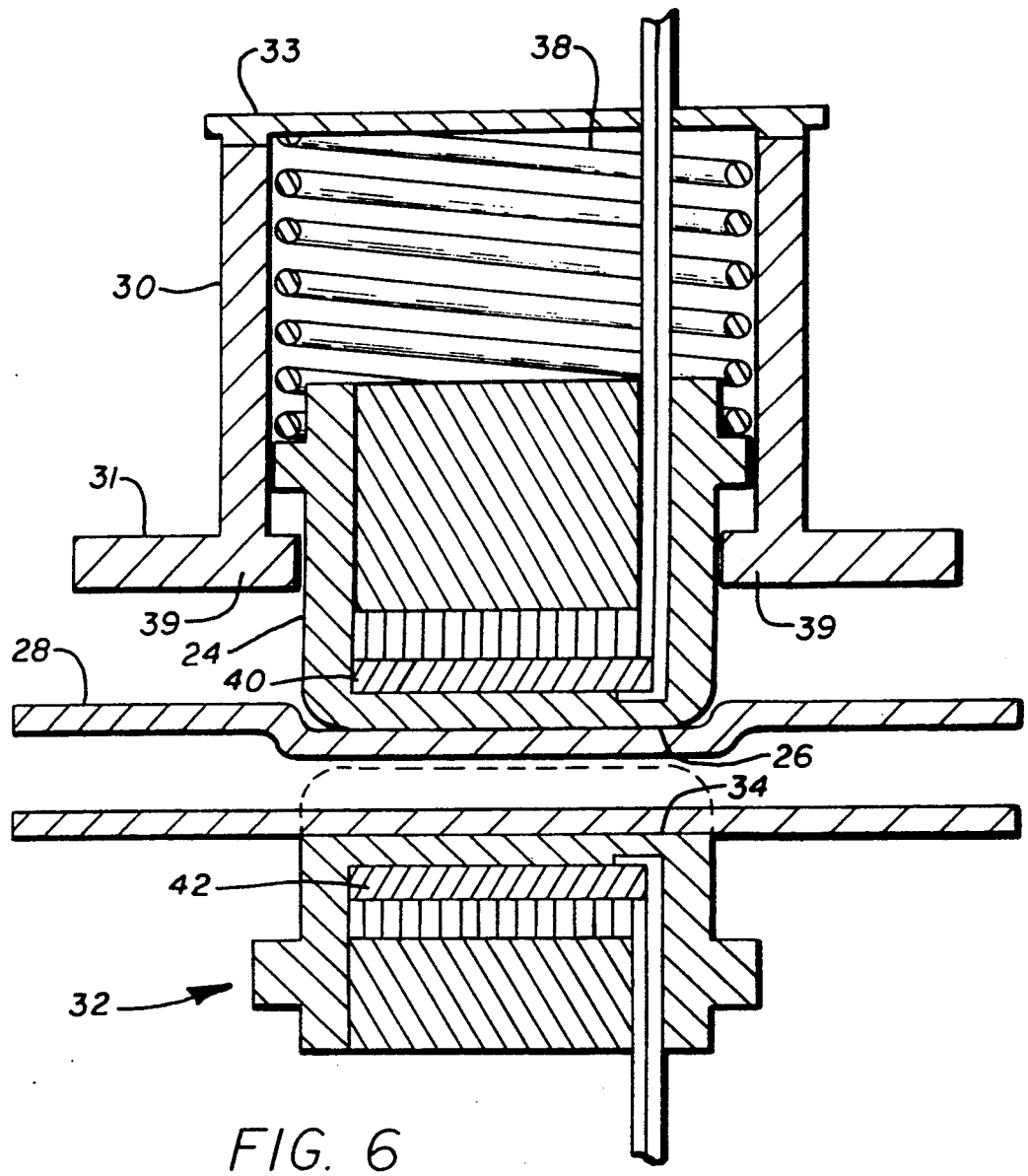
FIG. 6 is a cross-sectional view of an air-in-line sensor engaged with the fluid line as in FIG. 5 at an angle of 90° from the view of FIG. 5.

Referring now to FIG. 6, a view of the sensor of FIG. 5 from an angle of 90° is presented in cross section. The transducers 40 and 42 extend along a length of the fluid line and as shown the electrical feeds are mounted at one end.

In addition to providing for good transducer/fluid line contact, a two-part housing in accordance with the invention provides for ease in loading the fluid line into the sensor because of the channel in the second housing. This channeled housing may be mounted in the instrument below the pump as shown in FIG. 1. After the fluid line has been engaged with the vertically mounted peristaltic pump, gravity causes the succeeding portion of the fluid line to dispose itself in the channel. Closing the door results in the flat housing deforming the fluid line into the channeled housing thus controlling its position and causing firm contact with both transducers.

Although shown with a coil spring which biases the flat surface, other arrangements may be used. For example, a spring may be mounted to the channeled housing and the flat housing rigidly mounted. The arrangement shown in the figures is for purposes of illustration only. A material usable for the housing is ABS due to its favorable acoustic properties and flexible fluid line formed of polyvinyl chloride has been found to work well although other flexible materials may work equally well.

From the foregoing, it will be appreciated that the in-line fluid monitor system and method in accordance with the principles of the invention provide a simple, cost effective, and accurate way of detecting discontinuities in fluid in a fluid line. The fluid line may be disposable while the air-in-line sensor system can be reused.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

We claim:

1. An apparatus for monitoring fluid flow through a fluid line, the apparatus comprising:
    a first housing having a substantially flat engaging surface;
    a first transducer mounted in the first housing and coupled to the flat engaging surface;
    a second housing having a rectangular U-shaped channel formed therein to receive the fluid line, the second housing being oriented so that the opening of the channel faces the flat engaging surface;
    a second transducer mounted in the second housing and coupled to the bottom of the channel; and a spring mounted to urge one of the housings towards the other housing and into contact with the fluid line to deform the fluid line between the two housings into the substantially rectangular cross section shape of the channel.

2. The apparatus of claim 1 wherein the spring is mounted to urge the flat surface of the first housing to press the fluid line into the channel to deform the fluid line into the rectangular shape of the channel.

3. The apparatus of claim 2 further including a mounting housing within which one housing is movably mounted and within which the spring is mounted to press against said housing and urge it outward from the mounting housing towards the fluid line and the other housing, the mounting housing being mounted at a fixed distance from the other housing.

4. The apparatus of claim 3 wherein the fixed distance is selected so that the first and second housings will have an air gap between them when the spring has urged said housing outward from the mounting housing as far as possible.

5. The apparatus of claim 3 wherein the mounting housing comprises a stop means for limiting the spring from urging said housing outward of the mounting housing beyond a predetermined point.

6. The apparatus of claim 3 wherein the first housing is slidably mounted in the mounting housing.

7. The apparatus of claim 1 wherein the channel depth is selected to be approximately one-half of the width of the fluid line when the fluid line has been deformed into a rectangular shape.

8. The apparatus of claim 1 further comprising a fluid line guide having a channel to receive the fluid line and being disposed such that its channel is aligned with the channel of the second housing.

9. The apparatus of claim 1 wherein the channel of the second housing is oriented such that two sides of the rectangle of the deformed fluid line are approximately perpendicular to the flat engaging surface and exert force against the engaging surface in opposition to the force of the spring to result in the deformed fluid line having the substantially rectangular cross section shape.

10. An apparatus for use in monitoring fluid flow through a fluid line, the apparatus comprising:
a first housing having a substantially flat engaging surface;
a first transducer mounted in the first housing and acoustically coupled to the flat engaging surface;
a second housing having a rectangular U-shaped channel formed therein to receive the fluid line, the second housing being oriented so that the opening of the channel faces the flat engaging surface and the sides of the channel are approximately perpendicular to the flat engaging surface;
a second transducer mounted in the second housing and acoustically coupled to the channel; and
biasing means for urging the first housing towards the second housing and into contact with the fluid line located between the housings to deform the fluid line into the substantially rectangular cross sectional shape of the channel.

11. The apparatus of claim 10 further including a mounting housing within which the first housing is movably mounted and within which the spring is mounted to press against the first housing and urge it outward from the mounting housing towards the fluid line and the second housing, the mounting housing being mounted at a fixed distance from the second housing.

12. The apparatus of claim 11 wherein the fixed distance is selected so that the first and second housings will have an air gap between them when the spring has urged the first housing outward from the mounting housing as far as possible.

13. The apparatus of claim 11 wherein the mounting housing comprises a stop means for limiting the spring from urging said housing outward of the mounting housing beyond a predetermined point.

14. The apparatus of claim 11 wherein the first housing is slidably mounted in the mounting housing.

15. The apparatus of claim 10 further comprising a fluid line guide having a channel to receive the fluid line and being disposed such that its channel is aligned with the channel of the second housing.

16. A method of monitoring fluid flow through a fluid line comprising the steps of:
disposing the fluid line between a first housing having a flat engaging surface in contact with the fluid line and a second housing having a generally rectangular U-shaped channel in which the fluid line is disposed;
coupling a first transducer to the flat surface;
coupling a second tranducer to the channel;
urging one housing into contact with the fluid line to press the fluid line into the channel to deform the fluid line into the generally rectangular shape of the channel.

17. The method of claim 16 wherein the step of urging comprises coupling a spring to the first housing and urging said first housing to press the fluid line into the generally rectangular shape of the channel of the second housing.

18. The method of claim 16 further including the steps of:
slidably mounting the first housing in a mounting housing;
mounting a spring in the mounting housing and in contact with the first housing for urging the first housing outward of the mounting housing towards the fluid line and the second housing; and
mounting the mounting housing at a fixed distance from the second housing.

19. The method of claim 17 further comprising the steps of:
limiting the first housing from protruding beyond a predetermined distance outward of the mounting housing;
selecting the predetermined distance so that the first and second housings will have an air gap between them when the spring has urged said housing outward from the mounting housing as far as possible.

20. The method of claim 16 further comprising the step of aligning the fluid line with the channel of the second housing at a position external to the second housing.

* * * * *